(12) United States Patent
Asanuma et al.

(10) Patent No.: US 6,180,835 B1
(45) Date of Patent: Jan. 30, 2001

(54) PROCESS FOR THE PREPARATION OF CYCLOPROPYLACETYLENE DERIVATIVES

(75) Inventors: Goro Asanuma; Kazuya Takaki; Shigeo Ohzono; Manzo Shiono, all of Okayama-Pref. (JP)

(73) Assignee: Kuraray Co., Ltd., Kurashiki (JP)

(*) Notice: Under 35 U.S.C. 154(b), the term of this patent shall be extended for 0 days.

(21) Appl. No.: 09/245,305

(22) Filed: Feb. 5, 1999

(30) Foreign Application Priority Data

Feb. 6, 1998 (JP) .................................................. 10-025558
Mar. 19, 1998 (JP) .................................................. 10-069992

(51) Int. Cl.$^7$ .................................................. C07C 27/10

(52) U.S. Cl. .......................... 568/800; 549/416; 549/475; 556/482; 585/317; 585/534

(58) Field of Search .............................. 568/700; 549/416, 549/475; 556/482; 585/317, 534

(56) References Cited

U.S. PATENT DOCUMENTS

| 5,663,467 | * | 9/1997 | Thompson | 585/534 |
| 5,952,537 | * | 9/1999 | Stickley | 585/534 |
| 6,028,237 | * | 2/2000 | Parsons | 585/534 |
| 6,049,019 | * | 4/2000 | Fortunak | 585/534 |
| 6,072,094 | * | 6/2000 | Karady | 585/534 |

FOREIGN PATENT DOCUMENTS 1 531 578   7/1968   (FR) .

OTHER PUBLICATIONS

A.S. Thompson, et al., Tetrahedron Letters, vol. 36, No. 49, pp. 8937–8940, "Use of an Ephedrine Alkoxide to Mediate Enantioselective Addition of an Acetylide to a Prochiral Ketone: Asymmetric Synthesis of the Reverse Transcriptase Inhibitor L–743, 726", 1995.

W. Schoberth et al., Synthesis, p. 703, "Eine Einfache Herstellungmethode für Cyclopropylacetylen", Dec., 1972.

A.L. Henne, et al., J. Am. Chem. Soc., vol. 67, pp. 484–485, "Preparation and Physical Constants of Acetylenic Compounds", Mar., 1945.

M. Duchon D'Engenières, et al., Bulletin de la Socieété Chimique de France, No. 1, pp. 201–204, Alcoylation Sélective des Alcools Acétyléniques Dans L'ammoniac Liquide: Généralisation De La Méthode (4e Mémoire), with English Abstract, 1968.

(List continued on next page.)

*Primary Examiner*—Michael L. Shippen
(74) *Attorney, Agent, or Firm*—Oblon, Spivak, McClelland, Maier & Neustadt, P.C.

(57) ABSTRACT

A cyclopropylacetylene derivative of the formula (V):

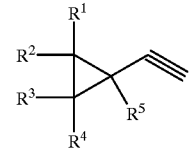

is prepared by reacting a propynol derivative of the formula (I):

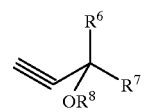

with a propane derivative of the formula (VI):

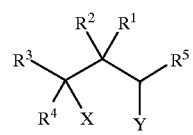

in the presence of a base in an amount of 2 or more equivalents relative to the propynol derivative to give a cyclopropane derivative of the formula (III):

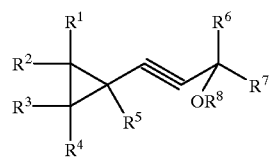

deprotecting the protecting group for the hydroxyl group of the cyclopropane derivative to give a cyclopropylpropynol derivative of the formula (IV):

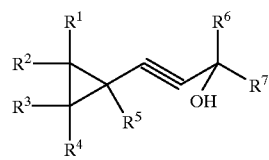

and subjecting the cyclopropylpropynol derivative to retro-ethynylation. In the above formulas $R^1$, $R^2$, $R^3$, $R^4$ and $R^5$ represent hydrogen; or an alkyl, alkenyl, aryl or aralkyl group, each of which may have a substituent, $R^6$ and $R^7$ is hydrogen; or an alkyl, alkenyl, aryl or aralkyl group, each of which may have a substituent, or $R^6$ and $R^7$ taken together form a ring, $R^8$ is a protecting group for the hydroxyl group and X and Y are each a leaving group.

18 Claims, No Drawings

OTHER PUBLICATIONS

O.M. Nefedov, et al., Organic Synthesis, Bulletin of the Academy of Sciences of the USSR, Division of Chemical Sciences, pp. 1164–1168, "Synthesis and Conversions of Cyclopropylacetylenes", 1978.

I.E. Dolgii, et al., Bulletin of the Academy of Sciences of the USSR. Division of Chemical science, vol. 34, pp. 1985–1986, "Synthesis of Cyclopropylethynyl Fulvene— The First Acetylenic Fulvene", 1985.

* cited by examiner

PROCESS FOR THE PREPARATION OF CYCLOPROPYLACETYLENE DERIVATIVES

BACKGROUND OF THE INVENTION

1. Field of the Invention

The present invention relates to a process for the preparation of a cyclopropylacetylene derivative, an intermediate for the synthesis of the cyclopropylacetylene derivative and a process for the preparation of the same. The cyclopropylacetylene derivative produced by the process of the present invention is useful as an intermediate in synthesis of a compound having a cyclopropane skeleton, for example, a benzoxazinone derivative (L-743726), which has anti-HIV activity (Tetrahedron Letters, Vol. 36, page 8937 (1995)).

2. Description of the Background

Recently, a large number of physiologically active substances having a cyclopropane skeleton have been discovered. Examples of known methods of producing cyclopropylacetylene, which is useful as an intermediate for the synthesis of these compounds, include: (I) a method in which 5-chloropentyne is reacted with n-butyllithium (Tetrahedron Letters, Vol. 36, page 8937 (1995)); and (2) a method in which cyclopropyl methyl ketone is reacted with phosphorus pentachloride in carbon tetrachloride to produce 1,1-dichloro-1-cyclopropylethane, which is subsequently dehydrochlorinated by potassium tert-butoxide (Synthesis page 703 (1972)).

However, in method (1), the yield of the raw starting material 5-chloropentyne in the reaction by which it is produced is as low as 57% (Journal of American Chemical Society, Vol. 67, page 484 (1945)), and method (2) gives many byproducts and, therefore, produces relatively low yields of the target product. Therefore, these methods are of limited industrial utility for the production of cyclopropylacetylene.

Another method by which cyclopropylacetylene is prepared requires the reaction of a propynol derivative with an alkyl (di)halide in liquid ammonia in the presence of lithium amide to give an acetylene derivative (Bulletin de la Societe Chimique de France, pages 201–204 (1968)). However, no method of transforming the obtained acetylene derivative to a compound having a cyclopropane skeleton is disclosed or suggested therein.

Another reaction which is known is the ethynylation of cyclopropylacetylene with acetone or cyclopropyl methyl ketone to give 2-methyl-4-cyclopropyl-3-butyn-2-ol or 2,4-dicyclopropyl-3-butyn-2-ol (Izvetiya Akademii Nark SSSR, Seriya Khimicheskaya, pages 1339–1344 (1978)), but no description for the reverse reaction is provided.

SUMMARY OF THE INVENTION

Accordingly, one object of the present invention is to provide a method by which a cyclopropylacetylene derivative can be produced in a good yield and by a commercially advantageous method.

Another object of the present invention is to provide an intermediate, which is useful in the production of a cyclopropylacetylene derivative.

Still another object of the invention is to provide a method of preparing the intermediate.

Briefly, these objects and other objects of the present invention as hereinafter will become more readily apparent can be attained by a cyclopropylacetylene derivative having formula (V):

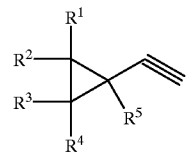

(V)

wherein each of $R^1$, $R^2$, $R^3$, $R^4$ and $R^5$ is hydrogen, or an alkyl, alkenyl, aryl or aralkyl group, each of which may have a substituent (hereinafter simply referred to as cyclopropylacetylene derivative (V)), which comprises the step of subjecting a cyclopropylpropynol derivative represented by the following formula (IV):

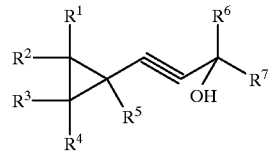

(IV)

wherein $R^1$, $R^2$, $R^3$, $R^4$ and $R^5$ have the same meanings as defined above and each of $R^6$ and $R^7$ represents hydrogen; or an alkyl, alkenyl, aryl or aralkyl group, each of which may have a substituent, or $R^6$ and $R^7$ together may form a ring (hereinafter simply referred to as cyclopropylpropynol derivative (IV)), to retroethynylation.

A second aspect of the present invention is a process for the preparation of cyclopropylacetylene derivative (V), by the steps of: (i) reacting a propynol derivative of formula (I):

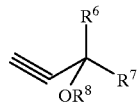

(I)

wherein $R^6$ and $R^7$ have the same meanings as defined above and $R^8$ is a protecting group for the hydroxyl group (hereinafter simply referred to as propynol derivative (I)) with a propane derivative having formula (VI):

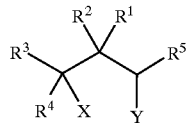

(VI)

wherein $R^1$, $R^2$, $R^3$, $R^4$ and $R^5$ have the same meanings as defined above, and each of X and Y is a leaving group (hereinafter simply referred to as propane derivative (VI)), in the presence of a base in an amount of less than 2 equivalents relative to the propynol derivative (1) at a temperature of 0° C. or lower to give an acetylene derivative having formula (II):

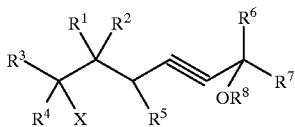

(II)

wherein $R^1$, $R^2$, $R^3$, $R^4$, $R^5$, $R^6$, $R^7$, $R^8$ and X have the same meanings as defined above (hereinafter simply referred to as acetylene derivative (II)), (ii) reacting the acetylene derivative (II) obtained with a base to give a cyclopropane derivative having formula (III):

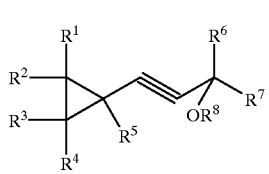

(III)

wherein $R^1$, $R^2$, $R^3$, $R^4$, $R^5$, $R^6$, $R^7$ and $R^8$ have the same meanings as defined above (hereinafter simply referred to as cyclopropane derivative (III)), (iii) removing the protecting group for the hydroxyl group of the obtained cyclopropane derivative (III) to give a cyclopropylpropynol derivative (IV), and (iv) subjecting the obtained cyclopropylpropynol derivative (IV) to retro-ethynylation.

A third aspect of the invention is a process for the preparation of a cyclopropylacetylene derivative (V), which comprises the steps of reacting a propynol derivative (I) with a propane derivative (VI) in the presence of a base in an amount of 2 or more equivalents relative to the propynol derivative (I) to give a cyclopropane derivative (III), removing the protecting group for the hydroxyl group of the obtained cyclopropane derivative (III) to give a cyclopropylpropynol derivative (IV), and subjecting the obtained cyclopropylpropynol derivative (IV) to retroethynylation.

A fourth aspect of the present invention is a process for the preparation of a cyclopropane derivative (III), which comprises the step of reacting an acetylene derivative (II) with a base.

A fifth aspect of the invention is a process for the preparation of a cyclopropane derivative (III), which comprises the step of reacting a propynol derivative (I) with a propane derivative (VI) in the presence of a base in an amount of 2 or more equivalents relative to the propynol derivative (I).

Finally, a sixth aspect of the invention is a cyclopropane derivative of formula (III-1):

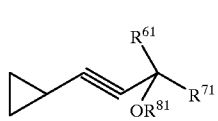

(III-1)

wherein $R^{61}$ is alkyl, $R^{71}$ is an alkyl group having 2 or more carbon atoms when $R^{61}$ is methyl or $R^{71}$ is alkyl when $R^{61}$ is an alkyl group having 2 or more carbon atoms, and $R^{81}$ is hydrogen or a protecting group for the hydroxyl group.

DETAILED DESCRIPTION OF THE PREFERRED EMBODIMENTS

Examples of the alkyl groups of groups $R^1$, $R^2$, $R^3$, $R^4$, $R^5$, $R^6$ and $R^7$ in the above formulae include methyl, ethyl, propyl, isopropyl, butyl, isobutyl, tert-butyl, 4-methylpentyl and the like. These alkyl groups each may have a substituent and examples of such substituents include hydroxy; methoxy, ethoxy, propoxy, butoxy and other alkoxyl groups; tert-butyldimethylsilyloxy, tert-butyldiphenylsilyloxy and other tri-substituted silyloxy groups; and phenyl, p-methoxyphenyl, p-chlorophenyl and other aryl groups.

The alkyl groups of $R^{61}$ and $R^{71}$ include, for instance, methyl, ethyl, propyl, isopropyl, butyl, isobutyl, tert-butyl, 4-methylpentyl and the like.

Examples of the alkenyl groups of substituents $R^1$, $R^2$, $R^3$, $R^4$, $R^5$, $R^6$ and $R^7$ include vinyl, propenyl and butenyl, and examples of the aryl groups include phenyl and naphthyl, for example. Examples of the aralkyl groups include benzyl, for instance. These alkenyl groups, aryl groups and aralkyl groups each may have a substituent, and examples of such substituents include hydroxyl; methyl, ethyl, propyl, butyl and other alkyl groups; methoxy, ethoxy, propoxy, butoxy and other alkoxyl groups; tert-butyldimethylsilyloxy, tert-butyldiphenylsilyloxy and other tri-substituted silyloxy groups; and phenyl, p-methoxyphenyl, p-chlorophenyl and other aryl groups.

Examples of the ring which is formed by $R^6$ and $R^7$ taken together include cyclopentane, cyclohexane, cycloheptane, cyclooctane and the like.

The protecting groups for the hydroxyl group of $R^8$ and $R^{81}$ include, for example, trimethylsilyl, tert-butyldimethylsilyl, tert-butyldiphenylsilyl and other tri-substituted silyl groups; 1-ethoxy-1-ethyl, tetrahydrofuranyl, tetrahydropyranyl and other acetal groups.

Examples of the leaving groups X and Y include chlorine, bromine, iodine and other halogen atoms; methanesulfonyloxy, ethanesulfonyloxy, benzenesulfonyloxy, p-toluenesulfonyloxy and other organic sulfonyloxy groups.

An embodiment of a process of synthesis of the present invention is in stepwise detail below.

Step 1:

In step 1 an acetylene derivative (II) or a cyclopropane derivative (III) is prepared by reacting a propynol derivative (I) with a propane derivative (VI) in the presence of a base The leaving groups on the 1- and 3-positions of the propane derivative (VI) may be identical or different. The use of leaving groups having different leaving properties is preferable to avoid an excessive reaction. Suitable propane derivative (VI) having such properties include 1-bromo-3-chloropropane, 1-iodo-3-chloropropane, 1-iodo-3-bromopropane 1-methanesulfonyloxy-3-chloropropane, 1-p-toluenesulfonyloxy-3-chloropropane or the like. Among them 1-bromo-3-chloropropane is typically preferred because of its availability.

Suitable bases for the reaction include methyllithium, n-butyllithium, sec-butyllithium, tert-butyllithium and other alkyllithium compounds; phenyllithium and other aryllithium compounds: methylmagnesium chloride, ethylmagnesium bromide and other alkylmagnesium halides; lithium amide, sodium amide, potassium amide, lithium diethylamide, lithium diisopropylamide, lithium bistrimethylsilylamide, sodium bistrimethylsilylamide, potassium bistrimethylsilylamide, bromomagnesium diisopropylamide and other metal amides; lithium methoxide, sodium methoxide, potassium methoxide, sodium ethoxide, potassium ethoxide, sodium tert-butoxide, potassium tert-butoxide and other metal alkoxides; sodium hydride, potassium hydride and other alkali metal hydrides and others.

When the amount of the base is 2 or more equivalents, preferably from 2 equivalents to 10 equivalents, relative to the propynol derivative (I), a cyclopropane derivative (III) is predominantly obtained. On the other hand, when a reaction is conducted using less than 2 equivalents, preferably 1 or more equivalent and less than 2 equivalents of the base relative to the propynol derivative (I) at a reaction temperature of 0° C. or lower, preferably −40° C. or lower, an acetylene derivative (II) is predominantly obtained.

The reaction may usually be conducted in any solvent as long as it does not adversely affect the reaction. Examples of the solvent include diethyl ether, tetrahydrofuran, dimethoxyethane and other ethers; pentane, hexane, heptane, octane, petroleum ether, benzene, toluene, xylene and other hydrocarbons; N,N-dimethylformamide, N-methylpyrrolidone, 1,3-dimethyl-2-imidazolidinone, hexamethylphosphoric triamide and other amides; dimethyl sulfoxide; ammonia; methylamine, ethylamine, propylamine, butylamine, diethylamine, ethylenediamine, N,N,N',N'-tetramethylethylenediamine and other amines; or mixtures of these solvents. The amount of the solvent employed is preferably within the range from 1 to 200 times as much as the weight of the propynol derivative (I).

The reaction is carried out by reacting a base with a mixture of a propynol derivative (I) and a solvent under an inert gas atmosphere and subsequently adding a propane derivative (VI) to the resulting mixture. The reaction temperature preferably ranges from −100° C. to 100° C., more preferably from −50° C. to 30° C. for the purpose of preparing cyclopropane derivative (III).

The prepared acetylene derivative (II) or cyclopropane derivative (III) can be isolated and purified in the usual manner for isolation and purification of organic compounds. By way of illustration, the reaction mixture is poured into water, aqueous ammonium chloride solution or the like, subjected to extraction with an organic solvent such as diethyl ether, ethyl acetate or methylene chloride, and the extract is washed, if necessary, with an aqueous sodium bicarbonate solution, water, a saline solution or the like to remove any acidic substance and any water-soluble substance. The extract is then dried with anhydrous sodium sulfate, anhydrous magnesium sulfate or the like and thereafter concentrated. The crude product obtained can be, as necessary, purified by distillation, chromatography, recrystallization or the like. However, the crude product can be employed without purification for the next reaction.

Step 2:

In step 2 a cyclopropane derivative (III) is prepared by reacting an acetylene derivative (II) with a base. Suitable bases include methyllithium, n-butyllithium, sec-butyllithium, tert-butyllithium and other alkyllithium compounds; phenyllithium and other aryllithium compounds; methylmagnesium chloride, ethylmagnesium bromide and other alkylmagnesium halides; lithium amide, sodium amide, potassium amide, lithium diethylamide, lithium diisopropylamide, lithium bistrimethylsilylamide, sodium bistrimethylsilylamide, potassium bistrimethylsilylamide, bromomagnesium diisopropylamide and other metal amides; lithium methoxide, sodium methoxide, potassium methoxide, sodium ethoxide, potassium ethoxide, sodium tert-butoxide, potassium tert-butoxide and other metal alkoxides; sodium hydride, potassium hydride and other alkali metal hydrides. The base is preferably used in an amount ranging from 1 equivalent to 3 equivalents relative to acetylene derivative (II).

Usually, a reaction may be conducted in any solvent as long as it has no adverse affect on the reaction. Suitable solvents include diethyl ether, tetrahydrofuran, dimethoxyethane and other ethers; pentane, hexane, heptane, octane, petroleum ether, benzene, toluene, xylene and other hydrocarbons; N,N-dimethylformamide, N-methylpyrrolidone, 1,3-dimethyl-2-imidazolidinone, hexamethylphosphoric triamide and other amides; dimethyl sulfoxide; ammonia; methylamine, ethylamine, propylamine, butylamine, diethylamine, ethylenediamine, N,N,N',N'-tetramethylethylenediamine and other amines; or mixtures of these solvents. The amount of the solvent employed preferably ranges from 1 to 200 times as much as the weight of acetylene derivative (II).

The reaction can be carried out under an inert gas atmosphere by adding a base to a mixture of an acetylene derivative (II) and a solvent or by adding an acetylene derivative (II) to a mixture of a base and a solvent. The reaction temperature preferably ranges from −100° C. to 100° C., more preferably −50° C. to 30° C. .

Thus cyclopropane derivative (III) prepared can be isolated and purified by the usual techniques employed for the isolation and purification of organic compounds. By way of example, the reaction mixture is poured into water, aqueous ammonium chloride solution or the like, and then extracted with an organic solvent such as diethyl ether, ethyl acetate, methylene chloride or the like. The extract obtained is washed, if necessary, with an aqueous sodium bicarbonate solution, water, a saline solution or the like to remove any acidic substance and any water-soluble substance. The extract is the dried with anhydrous sodium sulfate, anhydrous magnesium sulfate or the like and thereafter concentrated. The crude product prepared can be, as necessary, purified by distillation, chromatography, recrystallization or the like. However, the crude product may be used directly for the next reaction.

Step 3:

In step 3 a cyclopropylpropynol derivative (IV) is prepared by removing the protecting group for the hydroxyl group of a cyclopropane derivative (III)

When the protecting group for the hydroxyl group is a tri-substituted silyl group, cyclopropylpropynol derivative (IV) can be prepared by any commonly desilylation method. Such methods include a method of reacting cyclopropane derivative (III) with tetrabutylammonium fluoride in tetrahydrofuran, a method of reacting cyclopropane derivative (III) with hydrofluoric acid in water, a method of reacting cyclopropane derivative (III) with acetic acid in water or in a solvent mixture of tetrahydrofuran and water, and a method of reacting cyclopropane derivative (III) with potassium carbonate in methanol. When the protecting group for a hydroxyl group is an acetal group, a cyclopropylpropynol derivative (IV) can be prepared by a commonly employed deacetalation method, including for example a method of reacting cyclopropane derivative (III) with an acid in an alcoholic solvent.

The reaction temperature employed preferably ranges from −100° C. to 100° C., more preferably from −30° C. to 70° C.

Thus cyclopropylpropynol derivative (IV) prepared can be isolated and purified by the usual techniques of isolating and purifying organic compounds. By way of illustration, after confirming the completion of the reaction and neutralizing an acid catalyst with a base such as sodium methoxide, the reaction mixture is poured into water, and subjected to extraction with an organic solvent such as diethyl ether, ethyl acetate or methylene chloride. The extract is washed, if necessary, with an aqueous sodium bicarbonate solution, water, a saline solution or the like in order to remove any acidic substance and any water-soluble substance. The extract is then dried with anhydrous sodium sulfate, anhydrous magnesium sulfate or the like and thereafter concentrated. The crude product prepared can be, as necessary, purified by distillation, chromatography, recrystallization or the like. The crude product may be used directly for the next reaction.

Step 4:

In step 4 a cyclopropylacetylene derivative (V) is prepared by subjecting a cyclopropylpropynol derivative (IV) to retro-ethynylation A suitable method for retro-ethynylation of a cyclopropylpropynol derivative (IV) involves reacting the compound with a base. Suitable bases include lithium hydroxide, sodium hydroxide, potassium hydroxide and other alkali metal hydroxides; magnesium hydroxide and other alkaline earth metal hydroxides; lithium carbonate, sodium carbonate, potassium carbonate and other carbonates; methyllithium, n-butyllithium, sec-butyllithium, tert-butyllithium and other alkyllithium compounds; phenyllithium and other aryllithium compounds; methylmagnesium chloride, ethylmagnesium bromide and other alkylmagnesium halides; lithium amide, sodium amide, potassium amide, lithium diethylamide, lithium diisopropylamide, lithium bistrimethylsilylamide, sodium bistrimethylsilylamide, potassium bistrimethylsilylamide, bromomagnesium diisopropylamide and other metal amides; lithium methoxide, sodium methoxide, potassium methoxide, sodium ethoxide, potassium ethoxide, sodium tert-butoxide, potassium tert-butoxide and other metal alkoxides; sodium hydride, potassium hydride and other alkali metal hydrides and the like. A catalytic amount of the base is sufficient to use. However, the amount of the base preferably ranges from 0.001 equivalent to 5 equivalents relative to the cyclopropylpropynol derivative (IV).

The reaction may be conducted in the presence or in the absence of a solvent. If a solvent is employed, the solvent selected is not specially limited as long as it does not adversely affect the reaction. Suitable solvents include, for instance, methanol, ethanol, propanol, isopropanol, butanol, sec-butanol, tert-butanol, n-octanol and other alcohols; diethyl ether, tetrahydrofuran, dimethoxyethane and other ethers; pentane, hexane, heptane, octane, petroleum ether, benzene, toluene, xylene and other hydrocarbons; N,N-dimethylformamide, N-methylpyrrolidone, 1,3-dimethyl-2-imidazolidinone, hexamethylphosphoric triamide and other amides; dimethyl sulfoxide; or mixtures of these solvents. The amount of solvent preferably ranges from 1 to 200 times as much as the weight of the cyclopropylpropynol derivative (IV).

The reaction is preferably carried out under an inert gas atmosphere. The reaction temperature is preferably ranges from −100° C. to 150° C., more preferably from −30° C. to 80° C. The reaction can also be conducted while distilling cyclopropylacetylene derivative (V) produced during the reaction.

Thus cyclopropylacetylene derivative (V) prepared can be isolated and purified by any usual technique for isolating and purifying organic compounds. By way of example, the reaction mixture is poured into water, and then subjected to extraction with an organic solvent such as diethyl ether, ethyl acetate or methylene chloride. If necessary, the extract is washed with an aqueous sodium bicarbonate solution, water, a saline solution or the like to remove any acidic substance and any water-soluble substance. The extract is then dried with anhydrous sodium sulfate, anhydrous magnesium sulfate or the like and thereafter concentrated, and the obtained crude product can be, as necessary, purified by distillation, chromatography, recrystallization or the like.

As described, the present invention provides a process whereby a cyclopropylacetylene derivative can be prepared in a good yield and advantageously on an industrial scale.

The propynol derivative (I) as a starting material in the above steps can be prepared by providing the hydroxyl group of propynol compound having the following formula:

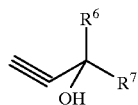

wherein $R^6$ and $R^7$ have the same meanings as defined above with a protecting group. Suitable such propynol compounds preferably include such available compounds as 2-methyl-2-hydroxy-3-butyne, 3-methyl-3-hydroxy-4-propyne, 2,6-dimethyl-6-hydroxy-7-octyne, 2,6-dimethyl-6-hydroxy-oct-2-en-7-yne or the like for their availability in an industrial scale operations.

The reaction described above of protecting the hydroxyl group of the propynol compound can be conducted in the following manner: For example, the hydroxyl group can be protected by a tri-substituted silyl group by reacting a tri-substituted silyl halide such as trimethylchlorosilane, tert-butyldimethylchlorosilane or tert-butyldiphenylchlorosilane with the propynol compound in the presence of an organic base such as triethylamine or pyridine. On the other hand, an acetal group as a protecting group for a hydroxyl group can be introduced by reacting a vinyl ether compound such as ethyl vinyl ether, 2,3-dihydrofuran or 3,4-dihydropyran with the propynol compound in the presence of an acid catalyst such as p-toluenesulfonic acid dihydrate, pyridinium p-toluenesulfonate, concentrated sulfuric acid or phosphoric acid.

Having generally described this invention, a further understanding can be obtained by reference to certain specific examples which are provided herein for purposes of illustration only and are not intended to be limiting unless otherwise specified.

EXAMPLE 1

A dried flask (200 ml volume), the inside of which had been flushed with nitrogen, was cooled to −50° C. Gaseous ammonia was then introduced into the cooled flask to give about 100 ml of condensed liquid ammonia. To the condensed ammonia was added 4.60 g (0.20 mol.) of lithium amide. To the mixture were added 7.70 g (0.05 mol.) of 2-methyl-2-tetrahydrofuranoxy-3-butyne and 20 ml of tetrahydrofuran at a temperature of −50° C. to −40° C. and the mixture was stirred for 30 minutes at the same temperature. After adding 9.45 g (0.06 mol.) of 1-bromo-3-chloropropane and 10 ml of tetrahydrofuran to the mixture, the reaction mixture was warmed to 0° C. over 10 hours while allowing liquid ammonia to distill from the reaction mixture, which was then stirred at 0° C. for 2 hours in order to complete the reaction. After the completion of the reaction, the reaction mixture was poured into 200 ml of an aqueous saturated ammonium chloride solution, cooled by ice, which was then extracted with two 100 ml portions of diisopropyl ether. The extract was washed with an aqueous saturated sodium bicarbonate solution and a saturated saline solution, dried over anhydrous sodium sulfate and concentrated by distilling the solvent through a rotary evaporator to give 11.8 g of a crude product.

The crude product was purified by distillation under reduced pressure to give 2-methyl-2-tetrahydrofLuranoxy-4-cyclopropyl-3-butyne (9.10 g, purity 97.6%, yield 91.6%) with the following physical data:

Boiling point: 64–66° C./0.2–0.3 Torr $^1$H-NMR spectrum (270 MHZ, CDCl$_3$, TMS, ppm)δ 0.60–0.80 (m, 411), 1.40 (s, 3H), 1.47 (s, 3H), 1.20–1.30 (m, 1H), 1.70–2.05 (m, 4H), 3.75–4.00 (m, 2H), 5.60–5.70 (m, 1H).

EXAMPLE 2

A dried flask (200 ml volume), the inside of which had been flushed with nitrogen, was cooled to −50° C. Gaseous ammonia was then introduced into the cooled flask to give about 100 ml of condensed liquid ammonia, and to the ammonia was added 4.60 g (0.20 mol.) of lithium amide. To the mixture were added 11.2 g (0.05 mol.) of 2,6-dimethyl-6-tetrahydrofuranoxy-7-octyne and 20 ml of tetrahydrofuran at a temperature of −50° C. to −40° C., and the mixture was stirred for 30 minutes at the same temperature. After adding 9.45 g (0.06 mol.) of 1-bromo-3-chloropropane and 10 ml of tetrahydrofuran, the reaction mixture was warmed to 0° C. over 10 hours while allowing liquid ammonia to distill and then stirred at 0° C. for 2 hours in order to complete the reaction. After the completion of the reaction, the reaction mixture was added to 200 ml of an aqueous saturated ammonium chloride solution, cooled by ice, which was then subjected to extraction with two 100 ml portions of diisopropyl ether. The extract was washed with an aqueous saturated sodium bicarbonate solution and a saturated saline solution, dried over anhydrous sodium sulfate and concentrated by distilling the solvent through a rotary evaporator to give 14.8 g of a crude product.

The crude product was purified by distillation under reduced pressure to (give 2,6-dimethyl-6-tetrahydrofuranoxy-8-cyclopropyl-7-octyne (12.17 g, purity 98.5%, yield 90.8%) having the following physical data:

Boiling point: 84–86° C./0.2–0.3 Torr $^1$-NMR spectrum (270 MHZ, CDCl$_3$, TMS, ppm)δ 0.60–0.80 (m, 4H), 0.87 (d, 6H, J=6.4 Hz), 1.35 (s), 1.43 (s, 3H together with s of δ=1.35), 1.10–2.05 (m, 12H), 3.75–4.00 (m, 2H), 5.60–5.70 (m, 1H).

EXAMPLE 3

To a dried flask (500 ml volume), the inside of which had been flushed with nitrogen, were charged 15.4 g (0.10 mol.) of 2-methyl-2-tetrahydrofuranoxy-3-butyne, 150 ml of tetrahydrofuran and 20 ml of hexamethylphosphoric triamide, and the resulting mixture was cooled to −70° C. Subsequently, 65 ml of n-butyllithium (1.55 mol./l n-hexane solution, 0.10 mol.) was added to the mixture and the resulting mixture was stirred at 70° C. for 30 minutes. After adding 15.8 g (0.10 mol.) of 1-bromo-3-chloropropane, the reaction solution was warmed to 0° C. over 2 hours and further stirred at 0° C. for 2 hours to complete the reaction. After the completion of the reaction, the reaction mixture was added to 500 ml of an aqueous saturated ammonium chloride solution, cooled by ice, and then subjected to extraction with two 200 ml portions of ethyl acetate. The extract was washed with an aqueous saturated sodium bicarbonate solution and a saturated saline solution, dried over anhydrous sodium sulfate and concentrated by distillation of the solvent through a rotary evaporator to give 22.8 g of a crude product. The crude product was purified by distillation under reduced pressure to give 2-methyl-2-tetrahydrofuranoxy-7-chloro-3-heptyne (19.2 g, purity 97.0%, yield 80.8%) having the following physical data:

Boiling point: 75–77° C./0.3 Torr $^1$H-NMR spectrum (270 MHZ, CDCl$_3$, TMS, ppm)δ 1.43 (s, 3H), 1.49 (s, 3H), 1.70–2.05 (m, 6H), 2.41 (t, J=6.9 Hz, 2H), 3.65 (t, J=6.4 Hz, 2H), 3.75–4.00 (m, 2H), 5.60–5.70 (m, 1H).

EXAMPLE 4

To a dried flask (500 ml volume), the inside of which had been flushed with nitrogen, were charged 12.1 g (0.12 mol.) of diisopropylamine and 150 ml of tetrahydrofuran and the mixture was cooled to 0° C. To the cooled mixture was added 77 ml of n-butyllithium (1.55 mol./l n-hexane solution, 0.12 mol.), and the resulting mixture was stirred at 0° C. for 30 minutes. The resultant solution was then cooled to −70° C. and then 19.0 g (purity 97.0%, 0.08 mol.) of 2-methyl-2-tetrahydrofuranoxy-7-chloro-3-heptyne prepared in Example 3 was added dropwise thereto. After the completion of the addition, the reaction mixture was warmed to 0° C. over 2 hours and further stirred at 0° C. for 2 hours to complete the reaction. After the completion of the reaction, the reaction mixture was added to 500 ml of an aqueous saturated ammonium chloride solution, cooled by ice, which was then extracted with two 200 ml portions of ethyl acetate.

The extract was washed with an aqueous saturated sodium bicarbonate solution and a saturated saline solution, dried over anhydrous sodium sulfate and concentrated by distilling the solvent through a rotary evaporator to give 16.8 g of a crude product. The crude product was purified by distillation under reduced pressure to give 2-methyl-2-tetrahydrofuranoxy-4-cyclopropyl-3-butyne (13.6 g, purity 97.5%, yield 85.4%).

EXAMPLE 5

In a dried flask (300 ml volume), the inside of which had been flushed with nitrogen, were placed 2,6-dimethyl-6-tetrahydrofuranoxy-8-cyclopropyl-7-octyne (10.72 g, purity 98.5%, 0.04 mol.) prepared in Example 2, ethanol (100 ml) and pyridinium p-toluenesulfonate (5.4 mg). The resulting mixture was heated at 50° C. to 60° C. for 2 hours. After the reaction was completed, the reaction mixture was cooled to room temperature and to the mixture was added 10 mg of sodium methoxide (25% methanol solution). Ethanol was removed by distillation through a rotary evaporator. To the concentrate obtained was added 100 ml of water and the resulting mixture was subjected to extraction with two 100 ml portions of ethyl acetate. The extract was washed with an aqueous saturated sodium bicarbonate solution and a saturated saline solution, dried over anhydrous sodium sulfate and concentrated by distillation of the solvent through a rotary evaporator to give 10.1 g of a crude product. The crude product was purified by distillation under reduced pressure to give 2,6-dimethyl-6-hydroxy-8-cyclopropyl-7-octyne (7.33 g, purity 99.0%, yield 93.5%) having the following physical data:

Boiling point: 75–77° C./0.2–0.3 Torr

1H-NMR spectrum (270 MHZ, CDCl$_3$, TMS, ppm)δ 0.60–0.80 (m, 4H), 0.89 (d, 6H, J=6.4 Hz), 1.43 (s, 3H), 1.10–1.70 (m, 8H), 2.03 (brs, 1H).

EXAMPLE 6

In a dried flask (300 ml volume), the inside of which had been flushed with nitrogen, were placed 2-methyl-2- tetrahydrofuranoxy-4-cyclopropyl-3-butyne (13.4 g, purity 97.5%, 67.3 mmol.) prepared in Example 4, ethanol (120 ml) and pyridinium p-toluenesulfonate (6.7 mg), and the resulting mixture was heated at 50° C. to 60° C. for 1 hour. After completion of the reaction, the reaction mixture was cooled to room temperature, 10 mg of sodium methoxide (25% methanol solution) was added to the cooled mixture and ethanol was distilled through a rotary evaporator. To the concentrate obtained was added 100 ml of water, and the mixture was subjected to extraction with two 100 ml portions of ethyl acetate. The extract was washed with an aqueous saturated sodium bicarbonate solution and a saturated saline solution, dried over anhydrous sodium sulfate and concentrated by distillation of the solvent through a rotary evaporator to give 10.8 g of a crude product. The crude product was purified by silica gel column chromatography to give 2-methyl-2-hydroxy-4-cyclopropyl-3-butyne (7.84 g, purity 98.6%, yield 92.6%) having the following physical data:

$^1$H-NMR spectrum (270 MHz, CDCl$_3$, TMS, ppm)δ 0.60–0.80 (m, 4H), 1.15–1.30 (m, 1H), 1.48 (s, 6H). 2.00–2.10 (brs, 1H).

EXAMPLE 7

In a flask (300 ml volume) were placed 2-methyl-2-hydroxy-4-cyclopropyl-3-butyne (7.60 g, purity 98.6%, 60.4 mmol.) prepared in Example 6, octanol (70 ml) and sodium hydroxide (25 mg) and the resulting mixture was heated at an inner temperature of 100° C. to 120° C. for 2 hours, while distilling 7.20 g of a mixture of cyclopropylacetylene and acetone, produced during the reaction, from the reaction medium. To the distillate was added 50 ml of heptane and the mixture was washed with water to remove acetone, and the heptane layer was distilled again to give cyclopropylacetylene (3.65 g, purity 99.6%, yield 91.2%).

EXAMPLE 8

In a flask (300 ml volume) were placed 2,6-dimethyl-6-hydroxy-8-cyclopropyl-7-octyne (7.20 g, purity 99.0%, 36.7 mmol.) prepared in Example 5, toluene (70 ml) and sodium hydroxide (29 mg) and the resulting mixture was heated at an inner temperature of 100° C. to 120° C. for 2 hours, while distilling 25.0 g of a mixture of toluene and cyclopropylacetylene, produced in the reaction, from the reaction medium. This distillate was distilled again by a rectification apparatus to give cyclopropylacetylene (2.23 g, purity 99.7%, yield 91.7%).

Obviously, numerous modifications and variations of the present invention are possible in light of the above teachings. It is, therefore, to be understood that within the scope of the appended claims, the invention may be practiced otherwise than as specifically described herein.

The disclosures of Japanese priority application Nos. 10-025558 and 10-069992 filed Feb. 6. 1998 and Mar. 19, 1998 are hereby incorporated by reference into the present application.

What is claimed as new and is intended to be secured by Letters Patent is:

1. A process for the preparation of a cyclopropylacetylene compound of formula (V):

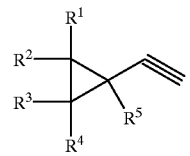

(V)

wherein each of $R^1$, $R^2$, $R^3$, $R^4$ and $R^5$ is hydrogen; or an alkyl, alkenyl, aryl or aralkyl group, each of which may have a substituent, which comprises the step of:

subjecting a cyclopropylpropynol compound of formula (IV):

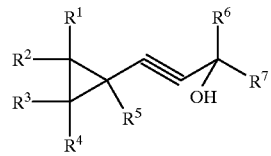

(IV)

wherein $R^1$, $R^2$, $R^3$, $R^4$ and $R^5$ have the same meanings as defined above, and each of $R^6$ and $R^7$ is hydrogen; or an alkyl, alkenyl, aryl or aralkyl group, each of which may have a substituent, or $R^6$ and $R^7$ taken together form a ring, to retro-ethynylation.

2. The process of claim 1, wherein said alkyl is methyl, ethyl, propyl, isopropyl, butyl, isobutyl, tert-butyl or 4-methylpentyl and the substituent for said alkyl is hydroxy; methoxy, ethoxy, propoxy, butoxy, tert-butyldimethylsilyloxy, tert-butyldiphenylsilyloxy, phenyl, p-methoxyphenyl or p-chlorophenyl.

3. The process of claim 1, wherein said alkenyl is vinyl, propenyl or butenyl, said aryl is phenyl or naphthyl and said aralkyl is benzyl and the substituent on these groups is selected from the group consisting of hydroxyl; methyl, ethyl, propyl, butyl, methoxy, ethoxy, propoxy, butoxy, tert-butyldimethylsilyloxy, tert-butyldiphenylsilyloxy, phenyl, p-methoxyphenyl or p-chlorophenyl.

4. A process for the preparation of a cyclopropylacetylene derivative of formula (V):

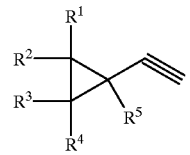

(V)

wherein each of $R^1$, $R^2$, $R^3$, $R^4$ and $R^5$ is hydrogen; or an alkyl, alkenyl, aryl or aralkyl group, each of which may have a substituent, which comprises the steps of:

reacting a propynol derivative of formula (I):

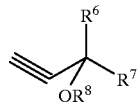

(I)

wherein each of $R^6$ and $R^7$ is hydrogen; or alkyl, alkenyl, aryl or aralkyl group, each of which may have a substituent, or $R^6$ and $R^7$ taken together form a ring, and $R^8$ is a protecting group for the hydroxyl group, with a propane derivative represented by formula (VI):

(VI)

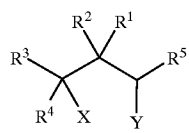

wherein $R^1$, $R^2$, $R^3$, $R^4$ and $R^5$ have the same meanings as defined above, and each of X and Y is a leaving group, in the presence of a base in an amount of less than 2 equivalents relative to the propynol derivative at a temperature of 0° C. or lower to give an acetylene derivative having formula (II):

(II)

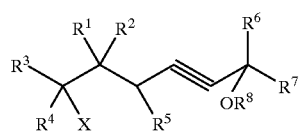

wherein $R^1$, $R^2$, $R^3$, $R^4$, $R^5$, $R^6$, $R^7$, $R^8$ and X have the same meanings as defined above, reacting said acetylene derivative with a base to give a cyclopropane compound having formula (III)

(III)

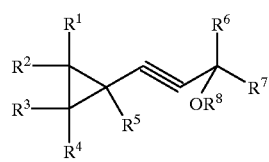

wherein $R^1$, $R^2$, $R^3$, $R^4$, $R^5$, $R^6$, $R^7$ and $R^8$ have the same meanings as defined above, removing the protecting group for the hydroxyl group of said cyclopropane derivative to give a cyclopropylpropynol derivative having formula (IV):

(IV)

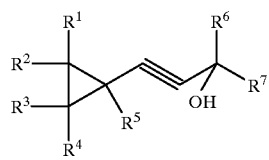

wherein $R^1$, $R^2$, $R^3$, $R^4$, $R^5$, $R^6$ and $R^7$ have the same meanings as defined above, and subjecting said cyclopropylpropynol derivative to retro-ethynylation.

5. The process of claim 4, wherein said alkyl is methyl, ethyl, propyl, isopropyl, butyl, isobutyl, tert-butyl or 4-methylpentyl and the substituent for said alkyl is hydroxy; methoxy, ethoxy, propoxy, butoxy, tert-butyldimethylsilyloxy, tert-butyldiphenylsilyloxy, phenyl p-methoxyphenyl or p-chlorophenyl.

6. The process of claim 4, wherein said alkenyl is vinyl, propenyl or butenyl, said aryl is phenyl or naphthyl and said aralkyl is benzyl and the substituent on these groups is selected from the group consisting of hydroxyl; methyl, ethyl, propyl, butyl, methoxy, ethoxy, propoxy, butoxy, tert-butyldimethylsilyloxy, tert-butyldiphenylsilyloxy, phenyl, p-methoxyphenyl or p-chlorophenyl.

7. A process for the preparation of a cyclopropylacetylene derivative having formula (V):

(V)

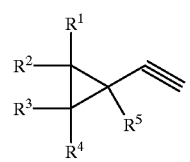

wherein each of $R^1$, $R^2$, $R^3$, $R^4$ and $R^5$ is hydrogen; or an alkyl, alkenyl, aryl or aralkyl group, each of which may have a substituent, which comprises the steps of:

reacting a propynol derivative of formula (I):

(I)

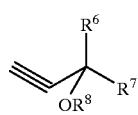

wherein each of $R^6$ and $R^7$ represents hydrogen; or an alkyl, alkenyl, aryl or aralkyl group, each of which may have a substituent, or $R^6$ and $R^7$ taken together form a ring, and $R^8$ is a protecting group for the hydroxyl group, with a propane derivative having formula (VI):

(VI)

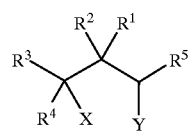

wherein $R^1$, $R^2$, $R^3$, $R^4$ and $R^5$ have the same meanings as defined above, and each of X and Y is a leaving group, in the presence of a base in an amount of 2 or more equivalents relative to the propynol derivative to give a cyclopropane derivative having formula (III):

(II)

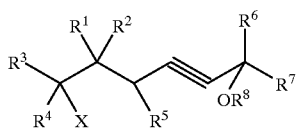

wherein $R^1$, $R^2$, $R^3$, $R^4$, $R^5$, $R^6$, $R^7$ and $R^8$ have the same meanings as defined above;

removing the protecting group for the hydroxyl group of said cyclopropane compound to give a cyclopropylpropynol derivative having formula (IV):

(IV)

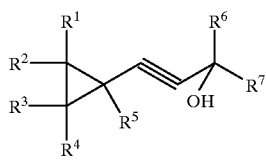

wherein $R^1$, $R^2$, $R^3$, $R^4$, $R^5$, $R^6$ and $R^7$ have the same meanings as defined above, and subjecting said cyclopropylpropynol derivative to retro-ethynylation.

8. The process of claim 7, wherein said alkyl is methyl, ethyl, propyl, isopropyl, butyl, isobutyl, tert-butyl or 4-methylpentyl and the substituent for said alkyl is hydroxy; methoxy, ethoxy, propoxy, butoxy, tert-butyldimethylsilyloxy, tert-butyldiphenylsilyloxy, phenyl, p-methoxyphenyl or p-chlorophenyl.

9. The process of claim 7, wherein said alkenyl is vinyl, propenyl or butenyl, said aryl is phenyl or naphthyl and said aralkyl is benzyl and the substituent on these groups is selected from the group consisting of hydroxyl; methyl, ethyl, propyl, butyl, methoxy, ethoxy, propoxy, butoxy, tert-butyldimethylsilyloxy, tert-butyldiphenylsilyloxy, phenyl, p-methoxyphenyl or p-chlorophenyl.

10. A process for the preparation of a cyclopropane derivative having formula (III):

(III)

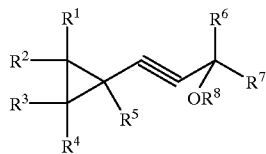

wherein each of $R^1$, $R^2$, $R^3$, $R^4$ and $R^5$ is hydrogen; or an alkyl, alkenyl, aryl or aralkyl group, each of which may have a substituent, each of $R^6$ and $R^7$ is hydrogen; or an alkyl, alkenyl, aryl or aralkyl group, each of which may have a substituent, or $R^6$ and $R^7$ taken together form a ring and $R^8$ is a protecting group for the hydroxyl group, which comprises the step of:

reacting an acetylene derivative having formula (II):

(II)

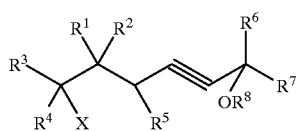

wherein $R^1$, $R^2$, $R^3$, $R^4$, $R^5$, $R^6$, $R^7$ and $R^8$ have the same meanings as defined above and X is a leaving group, with a base.

11. The process of claim 10, wherein said alkyl is methyl, ethyl, propyl, isopropyl, butyl, isobutyl, tert-butyl or 4-methylpentyl and the substituent for said alkyl is hydroxy; methoxy, ethoxy, propoxy, butoxy, tert-butyldimethylsilyloxy, tert-butyldiphenylsilyloxy, phenyl, p-methoxyphenyl or p-chlorophenyl.

12. The process of claim 10, wherein said alkenyl is vinyl, propenyl or butenyl, said aryl is phenyl or naphthyl and said aralkyl is benzyl and the substituent on these groups is selected from the group consisting of hydroxyl; methyl, ethyl, propyl, butyl, methoxy, ethoxy, propoxy, butoxy, tert-butyldimethylsilyloxy, tert-butyldiphenylsilyloxy, phenyl, p-methoxyphenyl or p-chlorophenyl.

13. A process for the preparation of a cyclopropane derivative having formula (III):

(III)

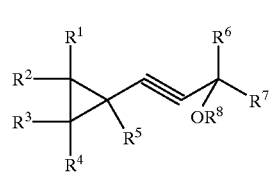

wherein each of $R^1$, $R^2$, $R^3$, $R^4$ and $R^5$ is hydrogen; or an alkyl, alkenyl, aryl or aralkyl group, each of which may have a substituent, each of $R^6$ and $R^7$ is hydrogen; or an alkyl, alkenyl, aryl or aralkyl group, each of which may have a substituent, or $R^6$ and $R^7$ taken together form a ring, and $R^8$ is a protecting group for the hydroxyl group, which comprises the step of:

reacting a propynol derivative having formula (I):

(I)

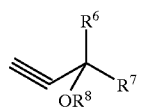

wherein $R^6$, $R^7$ and $R^8$ have the same meanings as defined above, with a propane derivative having formula (VI):

(VI)

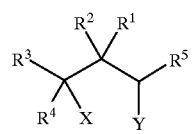

wherein $R^1$, $R^2$, $R^3$, $R^4$ and $R^5$ have the same meanings as defined above and each of X and Y is a leaving group, in the presence of a base in an amount of 2 or more equivalents relative to the propynol derivative.

14. The process of claim 13, wherein said alkyl is methyl, ethyl, propyl, isopropyl, butyl, isobutyl, tert-butyl or 4-methylpentyl and the substituent for said alkyl is hydroxy; methoxy, ethoxy, propoxy, butoxy, tert-butyldimethylsilyloxy, tert-butyldiphenylsilyloxy, phenyl, p-methoxyphenyl or p-chlorophenyl.

15. The process of claim 13, wherein said alkenyl is vinyl, propenyl or butenyl, said aryl is phenyl or naphthyl and said aralkyl is benzyl and the substituent on these groups is selected from the group consisting of hydroxyl; methyl, ethyl, propyl, butyl, methoxy, ethoxy, propoxy, butoxy, tert-butyldimethylsilyloxy, tert-butyldiphenylsilyloxy, phenyl, p-methoxyphenyl or p-chlorophenyl.

16. A cyclopropane derivative having formula (III-1):

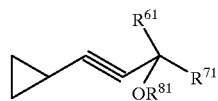
(III-1)

wherein $R^{61}$ is an alkyl group, $R^{71}$ is an alkyl group having 2 or more carbon atoms when $R^{61}$ is methyl, or $R^{71}$ is alkyl when $R^{61}$ is alkyl having 2 or more carbon atoms, and $R^{81}$ is hydrogen or a protecting group for the hydroxyl group.

17. The derivative of claim 16, wherein said protecting group of $R^{81}$ is trimethylsilyl, tert-butyldimethylsilyl, tert-butyldiphenylsilyl, 1-ethoxy-1-ethyl, tetrahydrofuranyl or tetrahydropyranyl.

18. The cyclopropane derivative as claimed in claim 16, wherein $R^{61}$ is methyl, $R^{71}$ is 4-methylpentyl and $R^{81}$ is a protecting group for the hydroxyl group in formula (III-1)

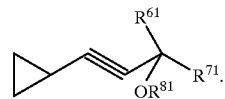
(III-1)

\* \* \* \* \*